United States Patent
Bergeron et al.

(10) Patent No.: US 8,534,319 B2
(45) Date of Patent: Sep. 17, 2013

(54) SERIAL SIPHON VALVES FOR FLUIDIC OR MICROFLUIDIC DEVICES

(75) Inventors: Michel G. Bergeron, Quebec (CA); Regis Peytavi, Cabestany (FR); Horacio Kido, Lake Forest, CA (US); Marc Madou, Irvine, CA (US)

(73) Assignees: Universite Laval, Quebec, Quebec (CA); The Regents of the University of California, Oakland, CA (US)

( * ) Notice: Subject to any disclaimer, the term of this patent is extended or adjusted under 35 U.S.C. 154(b) by 755 days.

(21) Appl. No.: 12/529,199

(22) PCT Filed: Mar. 3, 2008

(86) PCT No.: PCT/CA2008/000420
§ 371 (c)(1),
(2), (4) Date: Mar. 23, 2010

(87) PCT Pub. No.: WO2008/106782
PCT Pub. Date: Sep. 12, 2008

(65) Prior Publication Data
US 2011/0094600 A1    Apr. 28, 2011

Related U.S. Application Data

(60) Provisional application No. 60/904,372, filed on Mar. 2, 2007.

(51) Int. Cl.
*E03B 1/00* (2006.01)
(52) U.S. Cl.
USPC ............... 137/613; 137/38; 137/48; 137/628; 137/151; 137/825

(58) Field of Classification Search
USPC ....... 137/38, 48, 49, 613, 614, 628, 123–153, 137/825; 422/100, 103
See application file for complete search history.

(56) References Cited

U.S. PATENT DOCUMENTS

| | | | |
|---|---|---|---|
| 5,409,665 A | | 4/1995 | Burd |
| 5,518,930 A | * | 5/1996 | Burd .............................. 436/45 |
| 5,693,223 A | | 12/1997 | Yamada et al. |
| 5,693,233 A | * | 12/1997 | Schembri ...................... 210/787 |
| 6,143,248 A | | 11/2000 | Kellogg et al. |
| 6,620,478 B1 | * | 9/2003 | Ohman ........................ 428/64.1 |

(Continued)

FOREIGN PATENT DOCUMENTS

| | | |
|---|---|---|
| DE | 102005048233 A1 | 4/2007 |
| WO | 02/43866 A2 | 6/2002 |
| WO | 2006/093978 A2 | 9/2006 |

OTHER PUBLICATIONS

Stefan Haeberle, et al; "Microfluidic platforms for lab-on-a-chip applications", Lab Chip, 2007: DOI: 10.1039/b706364b, vol. 7, pp. 1094-1110 (see section III Centrifugal microfluidics), Received Apr. 26, 2007, Accepted Jun. 25, 2007.

*Primary Examiner* — Craig Schneider
*Assistant Examiner* — Jessica Cahill
(74) *Attorney, Agent, or Firm* — Ladas & Parry LLP

(57) ABSTRACT

Methods and devices using a co-radial arrangement of serial siphon structures composed of siphon valves each separated by a capillary valve to save radial space in a fluidic system. Such serial siphon valves allow to sequentially distribute liquids in a fluidic system upon application of successive centripetal accelerations and decelerations applied to a rotary platform.

11 Claims, 11 Drawing Sheets

(56) References Cited

U.S. PATENT DOCUMENTS

| | | |
|---|---|---|
| 6,752,961 B2 | 6/2004 | Kopf-Sill et al. |
| 2002/0106786 A1* | 8/2002 | Carvalho et al. ............ 435/287.3 |
| 2003/0044322 A1 | 3/2003 | Andersson et al. |
| 2004/0096867 A1* | 5/2004 | Andersson et al. ................ 435/6 |
| 2004/0120856 A1* | 6/2004 | Andersson et al. ............. 422/72 |
| 2005/0129583 A1* | 6/2005 | Bedingham et al. .......... 422/102 |
| 2005/0153431 A1* | 7/2005 | Andersson et al. ........ 435/287.2 |
| 2005/0202471 A1 | 9/2005 | Tooke et al. |
| 2005/0277195 A1* | 12/2005 | Holmquist et al. ............. 436/37 |

* cited by examiner

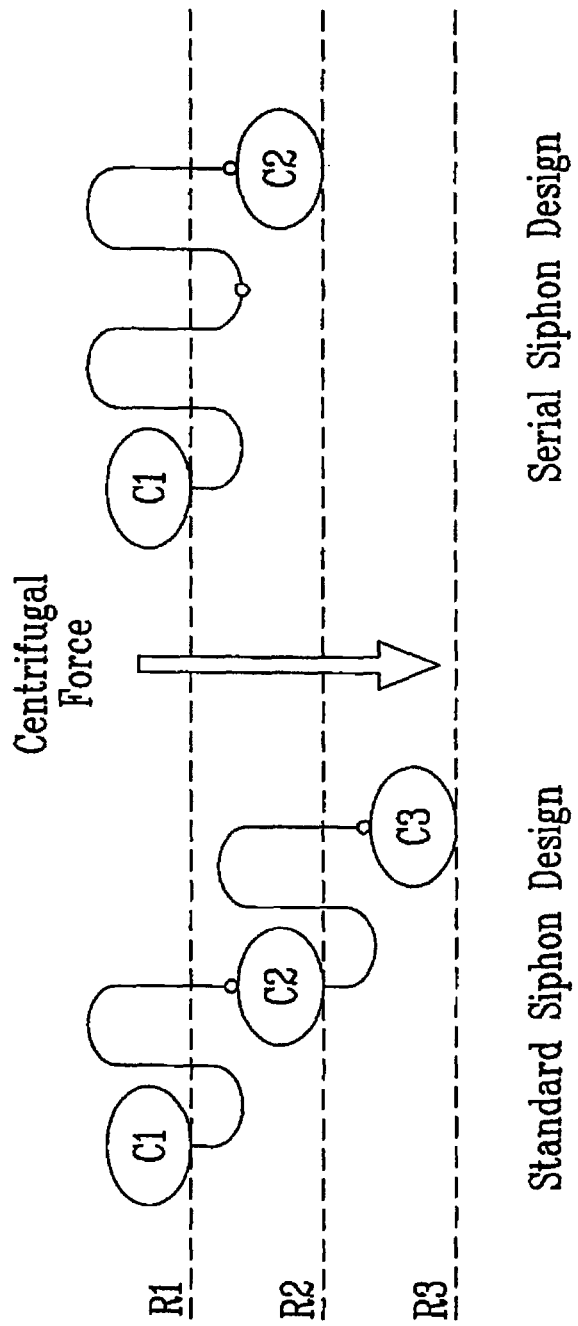

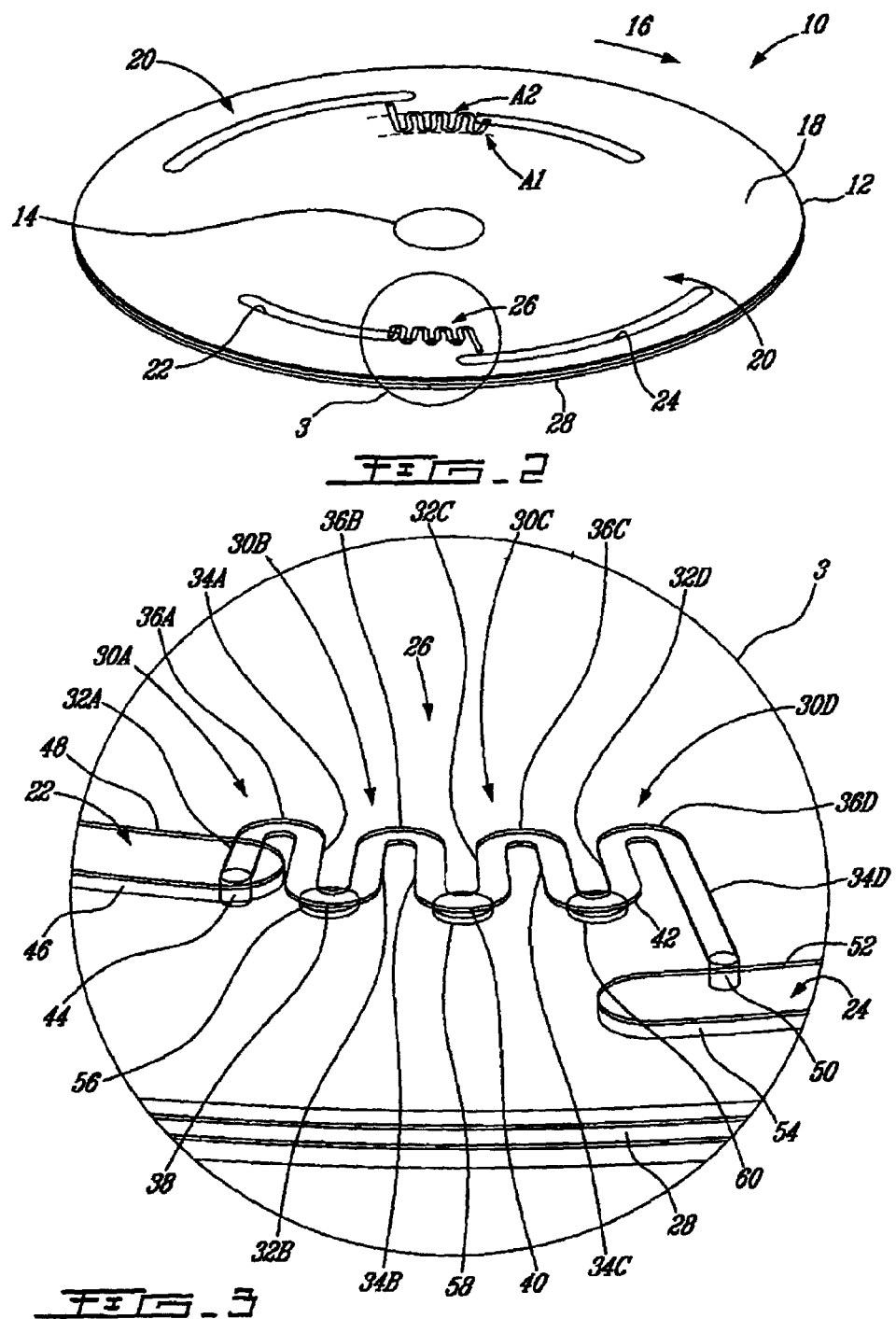

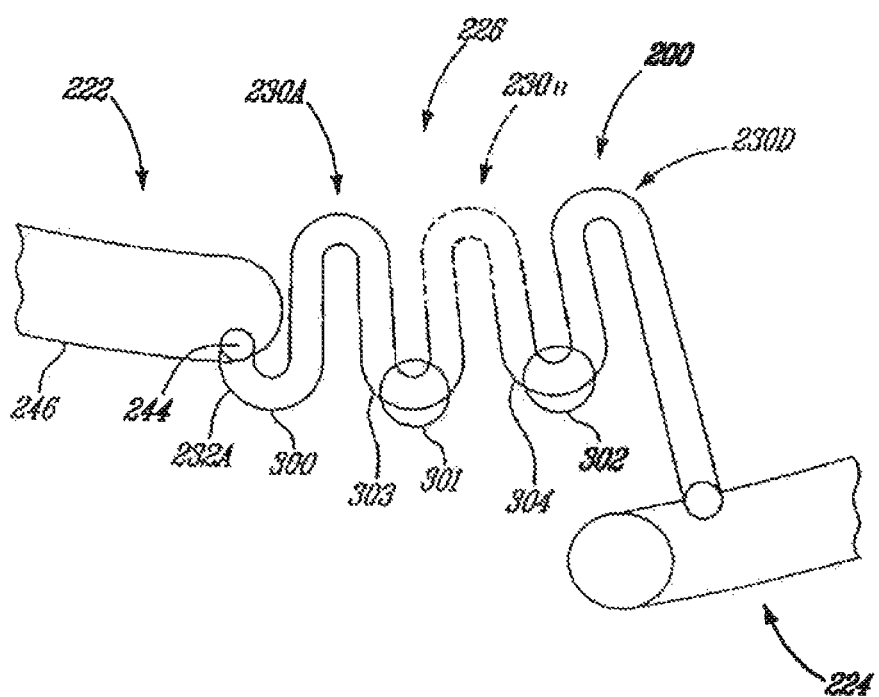
FIG_4

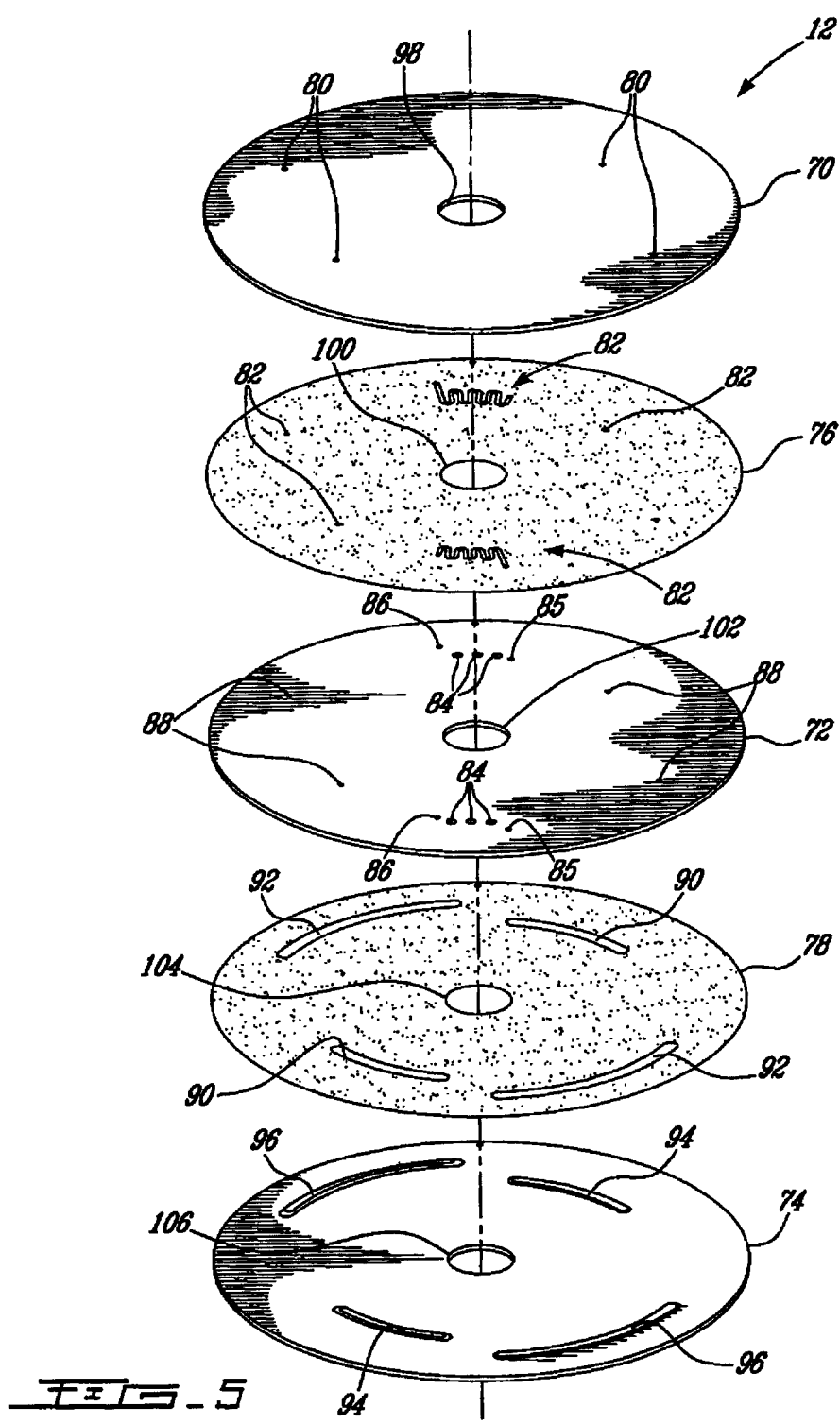

14 Seconds

16 Seconds

18 Seconds

24 Seconds

SERIAL SIPHON VALVES FOR FLUIDIC OR MICROFLUIDIC DEVICES

CROSS-REFERENCE TO RELATED APPLICATIONS

The present application requests priority on U.S. Provisional Application No. 60/904,372 filed in the United States Patent Office on Mar. 2, 2007 and incorporated herein by reference in its entirety.

FIELD OF INVENTION

The present invention relates to a fluidic device. More specifically but not exclusively, the present invention relates to serial siphon valves for a fluidic device.

BACKGROUND OF THE INVENTION

Control of the release of liquid from a fluidic chamber via a spinning rotor is a very important function in the area of centrifuged-based fluidic systems for applications such as immunoassays, nucleic acid analysis, biochemical tests, chemical tests and sample preparation. This is because it is often necessary to mix different reagents together at the appropriate time, either in parallel or in series.

Solutions to this problem include the use of rotational frequency-dependent burst valves, standard siphons, or mechanical valves. In general, burst valves are less reliable and thus have limited practical applications. As will be described herein, standard siphons (with in between chambers) work reliably but utilize precious space In the radial dimension of a rotor. Mechanical valves of all types necessarily require transduction systems that are complicated and not as reliable as siphons.

Centripetal force is commonly used to move small quantity of liquids into micro-channels (US 2005/0202471 A1; WO 2006/093978 A2). Because centripetal force is not affected by the characteristic of the liquid in terms of pH, salt concentration and to a lesser extent viscosity, it is a valuable force that can be used to move complex liquid samples such as biological samples into micro-channels.

Integration of complex functions on a microfluidic platform requires controllable valves. Most valves used in centripetal fluidic platforms are capillary valves (WO 98/07019). These valves burst at a precise centripetal acceleration applied by the rotor via the rotation of the disk. Valve bursting depends on the geometrical and surface characteristics of the fluidic system. By adjusting and optimizing their geometrical characteristics as well as their surfaces and distances from the center, one can sequentially move liquids from chambers/reservoirs to other chambers/reservoirs. Liquid constraint depends on the G-force applied to the system. When the centripetal G-force is higher than the capillary force, a capillary valve cannot prevent liquid movement within the system.

Some tasks, such as cell lysis and nucleic acid extraction, may require very high centripetal accelerations at the beginning of the protocol. Capillary valves, which are dependent on the G-force, will burst during such high centripetal accelerations. Therefore, capillary valves cannot be used to robustly delay liquid into a downstream chamber in such a system. A way to solve this problem is to use siphon valves. Siphon valves work as follows: An inverted U-shaped channel connects a given upstream dispensing chamber/reservoir to the next downstream receiving chamber/reservoir. The top of the inverted U (or top bend) is oriented toward the center of the rotor (radially inward) and is higher than the level of the liquid present in the upstream chamber. The inverted U-shaped channel has to be hydrophilic and small enough to provide capillary forces. During high centripetal acceleration, the centripetal forces prevent the capillary forces to prime the siphon (i.e. pass the inverted U top level and go lower than the bottom of the upstream chamber). When the centripetal acceleration is decreased below the capillary force, the siphon is primed. After priming, a higher centripetal acceleration will move the liquid from an upstream chamber/reservoir to a downstream chamber/reservoir.

Single siphon valves have been used in centrifugal fluidic devices in applications involving the separation of plasma from whole blood (Scott and Burtis, 1973, Analytical Chemistry, 45:327A-339A). They have also been used as a barrier to ensure the parallel, simultaneous, filling of a series of cuvettes on a rotor (U.S. Pat. No. 5,409,665), as well as in a rotor to transfer a dilution buffer from a holding chamber into a downstream chamber (U.S. Pat. No. 5,693,233). More recently, a rotor comprising siphons for delivering a premeasured volume of liquid between a first and a second chamber was designed (U.S. Pat. No. 6,752,961). This rotor used a sequence of alternating rotations and stops to effect the separation of plasma from whole blood, its dilution, and its distribution into a series of separate reaction cuvettes.

OBJECTS OF THE INVENTION

It is a non-limiting object of the present invention to provide a method using a co-radial arrangement of siphon structures each separated by a capillary valve in a fluidic system. Such a method allows saving radial space. This saved radial space can be used, for example, to add more features on a fluidic device.

It is a non-limiting object of the present invention to provide siphon structures that enable to sequentially distribute liquids in a fluidic system upon successive centripetal accelerations and decelerations applied to a rotary platform. Sequential fluid distribution can be controlled by the length and number of serial siphon structures.

It is a non-limiting object of the present invention to provide a device using a co-radial arrangement of siphon structures each separated by a capillary valve in a fluidic system. Such a device allows saving radial space. This saved radial space can be used, for example, to add more features on a fluidic device.

BRIEF SUMMARY OF THE INVENTION

In accordance with an aspect of the invention, there is provided a centripetal fluidic device comprising: a fluidic network comprising an upstream chamber, a downstream chamber, and a serial siphon valve conduit interposed therebetween and in fluid communication therewith at each respective opposite end thereof, the serial siphon valve conduit comprising a series of co-radial siphon valves separated by valve structures, wherein when applying a centripetal force to the fluidic network, a fluid within the network flows in the downstream direction.

In accordance with another aspect of the present invention, there is provided a centripetal fluidic device comprising: a fluidic network comprising an upstream chamber, a downstream chamber, and a serial siphon valve conduit interposed therebetween and in fluid communication therewith at each respective opposite end thereof, the serial siphon valve conduit comprising a series of siphon valves separated by valve structures, a given upstream siphon valve being directly in fluid communication with an adjacent downstream siphon valve via a valve structure interposed therebetween, wherein when applying a centripetal force to said fluidic network, a fluid within said network flows in the downstream direction.

In accordance with another aspect of the invention there is provided a centripetal fluidic device comprising: a fluidic network comprising an upstream chamber, a downstream chamber and a at least one siphon valve interposed therebetween and in fluid communication therewith, the siphon valve comprising a siphon structure in fluid communication with a capillary valve for blocking fluid movement at low G-force; wherein (a) when applying a centripetal force on the fluidic network, a fluid in the upstream chamber flows into the siphon structure; (b) when the centripetal force is greater than the capillary force of the at least one siphon valve, the fluid flows within the siphon structure for a distance determined by the fluid pressure therein being equal to the fluid pressure within the upstream chamber; (c) when the centripetal force is lesser than the capillary force, the fluid flows to the capillary valve and is stopped thereby, and (d) when a subsequent centripetal force is greater than the capillary force, the capillary valve is burst and the fluid flows towards the downstream chamber.

In accordance with a further aspect of the invention there is provided a centripetal fluidic device comprising: a fluidic network comprising an upstream chamber, a downstream chamber and a serial siphon valve conduit interposed therebetween and in fluid communication therewith at each opposite end thereof, the serial siphon valve conduit comprising a series of contiguous siphon valves separated by capillary valves for blocking fluid movement at low G-force; wherein (a) when applying a centripetal force on said fluidic network, a fluid in said upstream chamber flows into a first siphon valve; (b) when the centripetal force is greater than the capillary force of the first siphon valve, the fluid flows within the siphon valve for a distance determined by the fluid pressure therein being equal to the fluid pressure within the upstream chamber; (c) when the centripetal force is lesser than the capillary force, the fluid flows to the first capillary valve and is stopped thereby, and (d) when a subsequent centripetal force is greater than the capillary force the first capillary valve is burst and the fluid flows towards a subsequent siphon valve.

In accordance with yet another aspect of the invention there is provided a serial siphon valve conduit for a centripetally-motivated fluidic network having an upstream chamber and downstream chamber, the conduit comprising a series of co-radial siphon valves separated by capillary valves, the serial siphon valve conduit being connectable to the upstream and downstream chambers.

A method for sequentially distributing fluids in a centripetally-motivated fluidic system comprising: (a) providing a fluidic network comprising an upstream chamber, a downstream chamber, and a serial siphon valve conduit interposed therebetween and in fluid communication therewith at each respective opposite end thereof, said serial siphon valve conduit comprising at least one upstream siphon structure at least one downstream siphon structure separated by a capillary valve; (b) placing a fluid within the upstream chamber; (c) applying a centripetal force on the fluidic network so as to displace the fluid from said upstream chamber into the at least one upstream siphon structure; (d) decreasing the centripetal force below the capillary force intensity thereby moving the fluid in the siphon structure until it reaches the capillary valve; and (e) increasing the centripetal force above the capillary force thereby bursting the capillary valve. In an embodiment, this method further comprising: (f) reducing the centriperal force do as to all the fluid to prime the at least one downstream siphon structure after bursting the capillary valve.

In accordance with yet a further aspect of the invention there is provided a method for sequentially distributing fluids in a centripetally-motivated fluidic system comprising: providing a fluidic network comprising an upstream chamber, a downstream chamber, and a serial siphon valve conduit interposed therebetween and in fluid communication therewith at each respective opposite end thereof, said serial siphon valve conduit comprising a series of co-radial siphon valves separated by valve structures, placing a fluid within the upstream chamber; and applying a centripetal force on the fluidic network so as to displace the fluid from said upstream chamber into the serial siphon valve conduit.

In accordance with still another aspect of the invention there is provided a method for sequentially distributing fluids in a centripetally-motivated fluidic system comprising: providing a fluidic network comprising an upstream chamber, a downstream chamber and a at least one siphon valve interposed therebetween and in fluid communication therewith, said siphon valve comprising a siphon structure in fluid communication with a capillary valve for blocking fluid movement at low G-force; placing a fluid within the upstream chamber; and applying a centripetal force on the fluidic network so as to displace the fluid from said upstream chamber into the siphon valve.

In accordance with still a further aspect of the invention there is provided a method for sequentially distributing fluids in a centripetally-motivated fluidic system comprising: providing a fluidic network comprising an upstream chamber, a downstream chamber and a serial siphon valve conduit interposed therebetween and in fluid communication therewith at each opposite end thereof, said serial siphon valve conduit comprising a series of contiguous siphon valves separated by capillary valves for blocking fluid movement at low G-force; placing a fluid within the upstream chamber; and applying a centripetal force on the fluidic network so as to displace the fluid from said upstream chamber into the serial siphon valve conduit.

A non-limiting difference between the standard siphon system and the serial valve system, which is an object of the present invention, is the requirement for a central chamber between each siphon valve for the former.

A non-limiting difference between the standard siphon system and the present invention with that the series of siphon valves provide are arranged in a co-radial manner.

The documents referred to throughout are incorporated herein by reference in their entirety.

Other objects, advantages and features of the present invention will become more apparent upon reading of the following non-restrictive description of non-limiting illustrative embodiments thereof, given by way of example only with reference to the accompanying drawings

BRIEF DESCRIPTION OF THE FIGURES

Having thus generally described the invention, reference will be made to the accompanying figures, showing by way of illustration only an illustrative embodiment thereof and in which:

FIG. 1 illustrates standard siphon valves connecting a first and a second chamber versus the serial siphon valve system in accordance with an illustrative embodiment of the present invention;

FIG. 2 is a perspective view of the fluidic device in accordance with an illustrative embodiment of the present invention;

FIG. 3 is an enlarged view of portion 3 of FIG. 2;

FIG. 4 is a schematic view of a fluidic network in accordance with an illustrative embodiment of the present invention;

FIG. 5 is an exploded view of the fluidic device of FIG. 2;

DESCRIPTION OF ILLUSTRATIVE EMBODIMENTS

Figure 6:
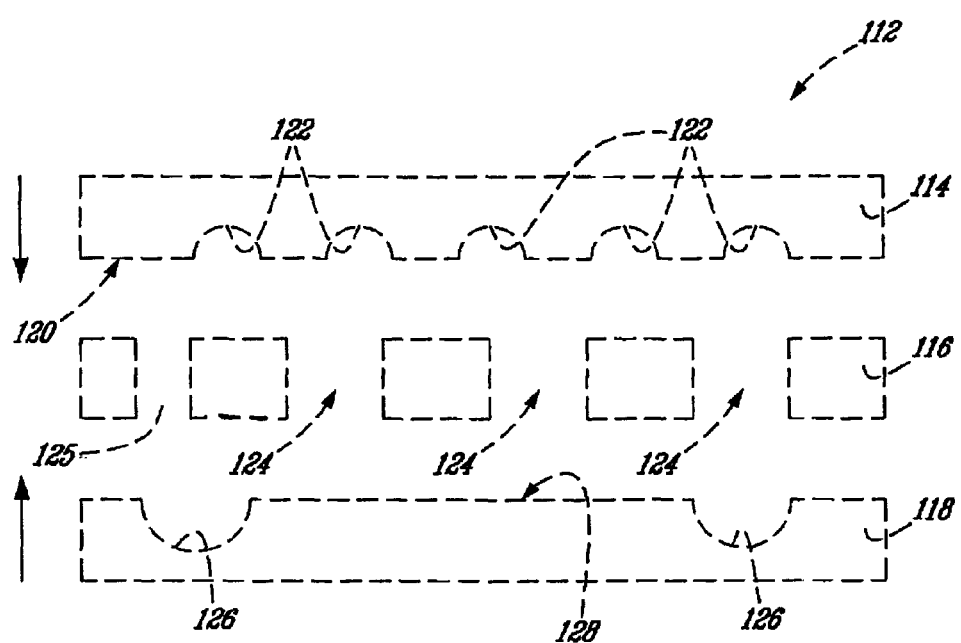
FIG. 6 is an exploded sectional schematic representation of a fluidic device in accordance with an illustrative embodiment of the present invention.

Generally stated, the present invention provides serial micro-valves actuated by capillary and centripetal forces for controlling the displacement of liquid into micro-channels from a chamber to another. The present invention also provides robust passive valves enabling complex integrations into a centripetal fluidic platform. In a specific non-exclusive example, this platform can be used for micro-total analysis systems (μTAS) dedicated for bioassays, chemical assays, and diagnostic assays.

Furthermore, the present invention provides a method to control minute volume of liquids centripetally-motivated into micro-channels. More precisely, the invention allows the sequential delivery of liquids from one reservoir/chamber to another chamber/reservoir using siphon valves. More particularly, this invention provides serial siphon valves enabling to apply successive centripetal accelerations and decelerations applied to a rotary platform in order to sequentially distribute liquids without the risk of unwanted valve bursting.

The serial siphon structures are composed of siphon valves separated from each other by a capillary valve (or stopper). When a first high centripetal acceleration is applied to the system, the liquid from the upstream chamber is blocked into the first siphon valve as soon as the liquid level in the siphon canal reaches the level of the liquid in the upstream chamber. When the centripetal acceleration is decreased below the capillary force intensity, the liquid in the siphon canal is moved by the capillary force until it reaches the first capillary valve (stopper) where the liquid stops. During the second high centripetal acceleration, the first stopper bursts but, because of high centripetal acceleration, the second siphon does not prime. Priming of the second siphon occurs only when the centripetal acceleration is reduced again. Priming of any subsequent siphon occurs based on the same principle.

As such, in the present invention, a co-radial arrangement of siphon structures, each separated by a capillary valve, obviates the need for a chamber between each siphon valve (designated "standard siphon valve" herein), thereby saving radial space.

The present invention provides an arrangement of siphons (or siphon valves) and capillary valves for the rotational-cycle dependent release of liquid within a centripetal fluidic platform in a way that minimizes the use of radial surface area. This is achieved by the use of centripetal force and capillarity of fluidic channels. A benefit that this arrangement has over standard siphons with in-between chambers is that it is more compact and it saves area in the radial dimension during cycles of rotating and stopping (see FIG. 1). In other words, this arrangement of siphons and capillary valves better preserves the potential energy of liquids during cycles of rotating and stopping than the standard siphon design. This ability is important when liquid reagents need to be released from upstream locations at specific times for use downstream on a centripetal fluidic device.

With general reference to FIG. 1, the present invention describes a system to control the release of fluid from an upstream chamber to a downstream chamber on a rotor by the use of co-radial siphon structures and capillary valves that enable to control the movement of liquids in a fluidic system by the use of alternating cycles of rotating and stopping (as illustrated in and as will be described with reference to FIGS. 7A-7J and 8). More specifically, FIG. 1 illustrates standard siphon valves connecting an upstream outlet or dispensing chamber to a downstream inlet or receiving chamber versus a serial siphon design in accordance with a non-limiting embodiment of the present invention. Initially, chambers C1 are filled in for both systems at radius R1. For the standard siphon design, a spin-stop-spin cycle allows the liquid to travel from C1 to C2 at radius R2, and then to C3 at radius R3. For the serial siphon design, the same spin-stop-spin cycle allows the liquid to move only from C1 to C2 at radius R2. Hence, the co-radial arrangement of the siphon structures obviates the need for a chamber between each siphon valve, thereby saving radial space. This is especially important in miniaturized centrifuged-based fluidic systems where the diameter of the rotor must be limited. This system is simple, and does not require the need for complicated external actuating mechanisms.

General Principle of Operation

It should be noted that the general principle of operation is generally based upon the principles of capillary wicking and valving. In the illustrated examples, the surface energy of the walls of the siphon was increased by exposure to oxygen plasma. This enables the spontaneous wicking of an aqueous solution into the siphon. The capillary valves are structures at which the approaching front of the liquid experiences a dramatic increase of contact angle, such that the liquid movement is stopped. When a G-force higher than the capillary force is produced in the siphon canal, the liquid is displaced into the siphon canal toward the center of the rotor until the pressure of the liquid column within the siphon canal is equal to the pressure of the liquid in the upstream chamber. When the G-force is reduced to a point where the capillary force becomes superior, the liquid primes the siphon and reaches the first capillary valve (the aforementioned stopper or blocker). At a low spinning rate, this valve constrains the liquid and avoids any unwanted priming of the second siphon. A subsequent high spin will burst the first capillary valve and force the liquid to reach pressure equilibrium into the canal of the second siphon. Cycles of spin and stop will therefore prime sequentially the different siphon valves of the serial siphon system. Considering that the G-force is applied uniformly to any column of liquid at a same distance from the center, equilibrium can be reached between the column of the liquid into the upstream chamber and the column of liquid into the siphon canal whatever the intensity and duration of the G-force applied to the system. Steps requiring high speed centrifugations such as cell debris clarification can then be achieved onto the rotary system during a spin and stop sequence.

Fluidic Device

FIG. 2 shows a fluidic device 10 in accordance with an illustrative embodiment of the present invention. In this particular embodiment, the fluidic device is a microfluidic centripetal device.

In the present example, the microfluidic centripetal device 10 is a microfluidic centripetal platform comprising a rotor in the form of a rotating disk 12. The rotating disk 12 includes a central hole 14 for receiving a rotary actuator (not shown) as is known in the art, which can spin the rotary disk 12 in the direction shown by arrow 16. The rotating disk 12 includes a main body or platform 18, including a fluidic network in the form of a microfluidic network 20 (for this non-limiting example). In this non-limiting example, there are two microfluidic networks 20; of course, a greater or lesser number can be contemplated within the scope of the present invention. Furthermore, a greater or lesser number of siphon structures can be contemplated within the scope of the present invention.

Turning to FIG. 3, the microfluidic network 20 includes an upstream dispensing chamber 22, a radially outwardly downstream receiving chamber 24 and a serial siphon valve conduit 26 therebetween. The dispensing and receiving chambers 22 and 24, respectively, are longitudinal curved structures formed in the body 18 of the disk 12 near the circumference 28 thereof.

The serial siphon valve conduit 26 comprises series of contiguous siphon valve structures 30A, 30B, 30C and 30D which are in fact portions of the conduit 26. The siphon valves 30A 30B, 30C and 300 are inverted U-shaped tunnels or canals and generally co-radial.

Each siphon valve 30A, 30B, 30C and 30D includes respective first and second branches in the form of a respective inlet siphon canal (32A, 32B, 32C, 320) and a respective outlet siphon canal (34A, 34B, 34C and 34D) respectively. Each siphon valve 30A, 30B, 30C and 30D includes a respective bend (i.e. the top of the inverted U-shape) 36A, 36B, 36C and 36D formed between its adjacent inlet and outlet siphon canals (32A, 32B, 32C, 32D) and (34A, 34B, 34C and 34D) respectively. The siphon valves 30A, 30B, and 30C are each contiguous the next adjacent siphon valve, namely 30B, 30C and 30D respectively by way of a respective bend 38, 40 and 42. More specifically, bend 38 is formed between canals 34A and 32B, bend 40 is formed between canals 34B and 32C and bend 42 is formed between canals 34C and 32D. The serial siphon valve conduit 26 includes an inlet aperture 44 formed at the free end of the siphon canal 32A and positioned within the dispensing chamber 22 near its outwardly radial wall 46 (as opposed to its inwardly radial wall 48). An outlet aperture 50 is formed at the opposite end of the serial siphon valve conduit 26 and is in fluid communication with the receiving chamber 24. Specifically in this example, the outlet aperture 50 is positioned near the inwardly radial wall 52 of the chamber 24 (as opposed to the outwardly radial wall 54).

In this way, the serial siphon valve conduit 26 has a sinuous or serpentine configuration between the inlet and outlet apertures 44 and 50, respectively, thereby defining inwardly radial bends 36A, 36B, 36C and 36D and outwardly radial bends 38, 40 and 42. The inwardly radial bends 36A, 36B, 36C and 36D are positioned generally along the same inner arc A1 (see FIG. 2) and the outwardly radial bends 38, 40 and 42 are positioned generally along the same outer arc A2 (see FIG. 2).

The serial siphon valve conduit 26 also includes valve structures 56, 58 and 60 which are capillary valves and which are respectively positioned at and contiguous with bends 38, 40 and 42. In fact, these capillary valves 56, 58 and 60, which are in the form of discs, enlarge the spatial structure of the bends 38, 40 and 42 respectively. In this way, the serial siphon valves 30A, 30B, 30C and 30D are separated by capillary valves 56, 58 and 60.

In this particular example each capillary valve 56, 58 and 60 is connected directly at the bottom of each U-shaped configuration joining adjacent valves, namely at bends 38, 40 and 42. However, persons skilled in the art may modify this design within the scope of the present invention. For example, the capillary valve can be connected to the lateral branches (the inlet or outlet canals) of the siphon valve.

It is understood that the terms canal, siphon canal, siphon, siphon valve, siphon conduit are used herein for indicative purposes only so as to more easily describe the illustrated structures and not limit the function of the present invention. Hence, the siphon valves 30A, 30B, 30C and 30D have a dual siphoning and valve function within the context of the invention as described herein. It should also be understood that the branched inlet and outlet canals as well as the bend interposed therebetween of each siphon valve 30A, 30B, 30C and 30D forms a respective siphon structure that is contiguous with a valve structure (such as a capillary valve). It should be further understood, that a series of siphon valves includes at least two siphon valves. If there are two siphon valves, the second siphon valve need not include a valve structure and as such this second siphon valve may be a siphon structure only. This is the case for siphon valve 30D which does not include a valve structure since it directly empties into the downstream chamber 24. Given the fact, that the siphon valves of the invention can include a siphon structure that is preceded by a valve yet not followed by a valve (such as siphon valve 30D in the Figures), the term "siphon valve" is also used. Of course, the foregoing is clearly illustrated in the accompanying drawings. The term "siphon valve" also refers to standard siphons (siphon structures) without the additional valves added by the present invention.

In one particular non-limiting example, the serial siphon valve conduit 26 is 1 mm wide and 0.1 mm deep; the upstream dispensing and downstream receiving chambers 22 and 24, respectively, are 0.6 mm deep; the capillary valves 56, 58 and 60, are 2 mm in diameter and 0.3 mm deep; and the whole disk 12 is 120 mm in diameter.

In the embodiment illustrated in FIGS. 2 and 3: the serial siphon valve conduit 26 includes four siphon valve, 30A, 30B, 30C and 30D; the first inlet canal 32A is configured to draw fluid towards the inwardly radial bend 36A; and the last outlet canal 34D is generally longer than the other canals 32A, 34A, 32B, 34B, 32C, 34C and 32D so as to extend to the downstream chamber 24. Of course other configurations can also be contemplated within the scope of the present invention.

For example, FIG. 4 shows another configuration of a microfluidic network 200 in accordance with an illustrative embodiment of the present invention.

The microfluidic network 200 includes an upstream dispensing chamber 222, and a downstream receiving chamber 224 as well as a serial siphon valve conduit 226 therebetween.

The serial siphon valve conduit 226 includes siphon structures or siphon valves 230A, 230n and 230D. The siphon valve 230n shown in dotted line represents the fact that a greater or lesser number of siphon valves can be included between the first and last siphon valves 230A or 230D respectively. The siphon valve 230A includes an inlet canal 232A having an inlet aperture 244 in fluid communication with the chamber 222 and being positioned at the outwardly radial wall 246 thereof. This canal 232A (as opposed to canal 32A) is configured to draw fluid in the outwardly radial direction relative to the camber 222 towards a first inwardly radial bend 300 which does not include a capillary valve such as valves 301 and 302 at bends 303 and 304 respectively.

Therefore, various configurations of the fluidic networks and serial siphon valve conduits of the invention can be contemplated within the scope of the invention.

It should be noted that the centripetal fluidic devices of the present invention can include a platform and as such the device is the platform or a plurality of like platforms, these devices may also include a platform and an actuator (not illustrated but known in the art) or a plurality of such platforms and an actuator or alternatively a plurality of such platforms with a plurality of actuators.

The Rotary Disk

With reference to FIG. 5, the platform or rotary disk 12 will be described In greater detail. In this example, the rotary disk 12 is in fact a stratified disk assembly.

Rotary disk assembly 12 therefore assembles three machined disk members, namely a first disk member 70, a second disk member 72 and a third disk member 74 as well as a pair of adhesive members, namely a first adhesive member 76 and a second adhesive member 78.

The disk member 70 serves as the cover and has drilled holes 80 for the purpose of input of liquid and output of air. The first adhesive member 76 serves to bond the first and second disks 70 and 72 respectively. The first adhesive member 76 includes cut openings 82 which define respective sinuous, serpentine or winding configurations. This sinuous configured opening 82 serves to define the serial siphon valve conduit 26 when the assembly 12 is assembled. The second disk member 72 has machined capillary valve openings 84 as which will define the capillary valves 56, 58 and 60. The second disk member 72 also includes an inlet hole 85 and an outlet hole 86 which when interfaced with the cut opening 82 provide the inlet and outlet apertures 44 and 50, respectively. The first adhesive member 76 and the second disk member 72 also include respective holes 87 and 88, which correspond to holes 80, for enabling the flow of liquid between different layers. The second adhesive member 78 bonds the second and third disk members 72 and 74 respectively and includes arch-shaped upstream and downstream formations 90 and 92, respectively, that are complementary to the upstream and downstream chamber grooves 94 and 96, respectively, that are machined into the third disk 74 for defining the upstream and downstream chambers 22 and 24, respectively. In another embodiment, the formations 90 and 92 are openings and the chambers 22 and 24 are formed between grooves 94 and 96 and the second disk 72. Similarly, the serial siphon conduit 26 and the capillary valves 56, 58 and 60 are formed between the disks 70 and 72 (with the second adhesive member 78 intervening or being otherwise open). Finally, the disk members 70, 72 and 74 and the adhesive members 76 and 78 include respective and complementary central holes 98, 100, 102, 104 and 106 that together form the central disk hole 14.

In one embodiment, before assembly, the first and second disks 70 and 72 are exposed to oxygen plasma for the purpose of increasing their surface energies and enabling the spontaneous wicking of aqueous solutions into the serial siphon valve conduit 26.

In one non limiting example, the first and second disk members 70 and 72 are each 0.6 mm thick, whereas the third disk member 74 is 1.2 mm thick and the first and second adhesive members 76 and 78 are each 0.1 mm thick, The disk 12 can be manufactured by several technologies including but not limited to: micromachining, hot embossing, injection molding, photolithography chemical etching, laser welding, ultra-sound bounding, thermal bounding, and chemical bounding.

The disk 12 which serves as the microfluidic platform can be provided in other suitable configurations or constructions within the scope of the present invention. A variety of disk members having various machined constructions, cuts or openings can be interfaced to create the microfluidic networks of the present invention.

For example, FIG. 6 is a schematic cross sectional (not to scale) representation of a disassembled disk assembly 112 comprising first, second and third members 114, 116 and 118 respectively. The first disk member 114 has a machined underface 120 defining grooves 122 that will provide the serial siphon valve conduit when assembled with the second and third disk members 116 and 118. The second disk member 116 includes openings 124 through its body that define the capillary valves between the first and third disk member 114 and 118. The second disk member 116 may also include other openings 125 to provide inlets or outlets example. Finally, the third disk member 118 includes machined grooves 126 in its top face 128 that define the upstream and downstream chambers when assembled to the first and second disk members 114 and 116. These disk members 114, 116 and 118 can be adhered together by various ways known in the art within the context of the present invention. It is understood that the components of FIG. 6 are shown in dotted line as to represent an embodiment rather than show proper alignment.

Of course a variety of other platform structures, configurations and processes of making can be contemplated by the skilled artisan within the scope of the present invention.

Non-Limiting Applications

The present invention may be used for any application that specifically requires the sequential flow of different liquids through a channel. For example, if a DNA microarray is immobilized in a channel or chamber, one may want to perform a hybridization step in which enzyme-labeled complementary DNA is made to flow through the channel in cycle 1. In cycle 2, one may want to wash with a buffer solution. Finally, a substrate solution specific for the enzyme used may follow in cycle 3. Another application might be the purification of DNA. One may use glass beads (for capturing DNA) in a channel. The sequential flow of a sample containing DNA with impurities, one or more wash buffer volumes, and an elution buffer could be conducted.

The present invention is illustrated in further detail by the following non-limiting example.

EXAMPLE 1

A Serial Arrangement of Siphon Valves in a Centripetal Fluidic Platform for Controlling the Release of Fluid FIGS. 7A to 7J illustrate the present invention in action. A non-limiting example of a corresponding spin profile is also shown in FIG. 8. More specifically, FIG. 8 illustrates the spin profile used to control the release of liquid L from an upstream chamber 22 into a downstream chamber 24 by the use of serial siphon microfluidic structures such as the serial siphon valve conduit 26.

Rotation at 1,500 RPM generates centrifugal acceleration that enables the liquid front to travel beyond the capillary valves. After about 24 seconds (see FIGS. 7J and 8), most of the liquid L from the upstream chamber 22 can be transferred to the downstream chamber 24. In this example a total of five cycles of rotation and stopping are demonstrated. The number of cycles that may be incorporated into this system would be limited by the liquid front's (F1, F2, F3, F4, F5, F6, F7, F8, F9, F10) ability to "pull" the increasing amount of liquid L behind it.

Figure 7A:
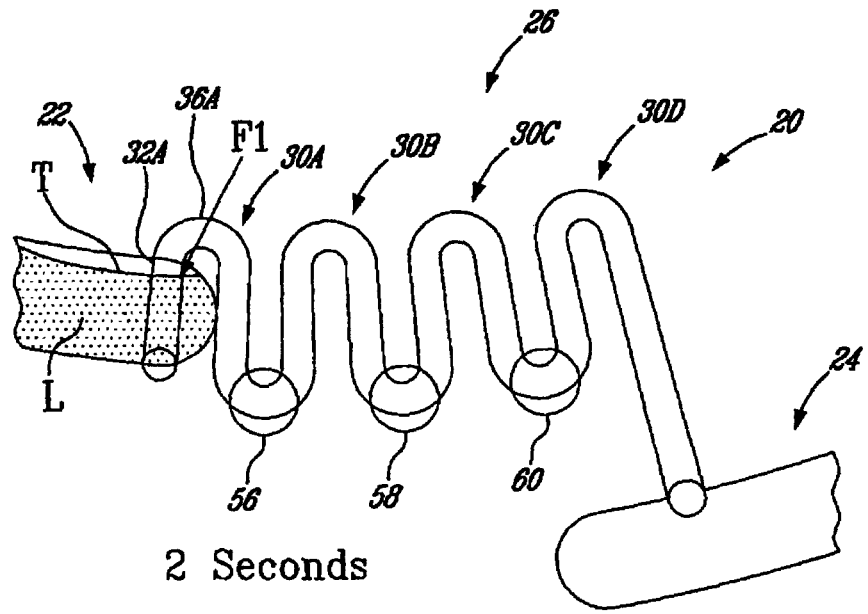
FIGS. 7A to 7J are sequential views of the present serial siphon valve system in action in accordance with an illustrative embodiment of the present invention.
Figure 7B:
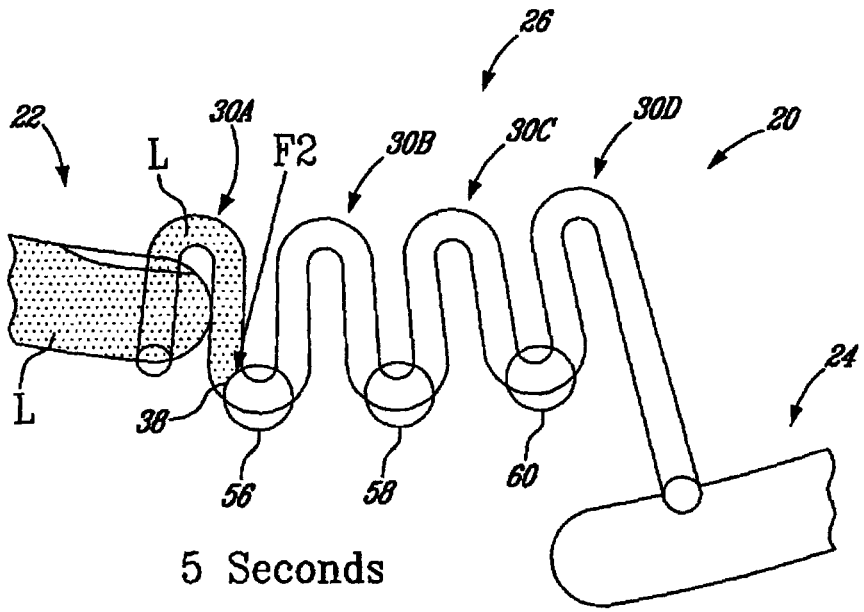
Figure 7C:
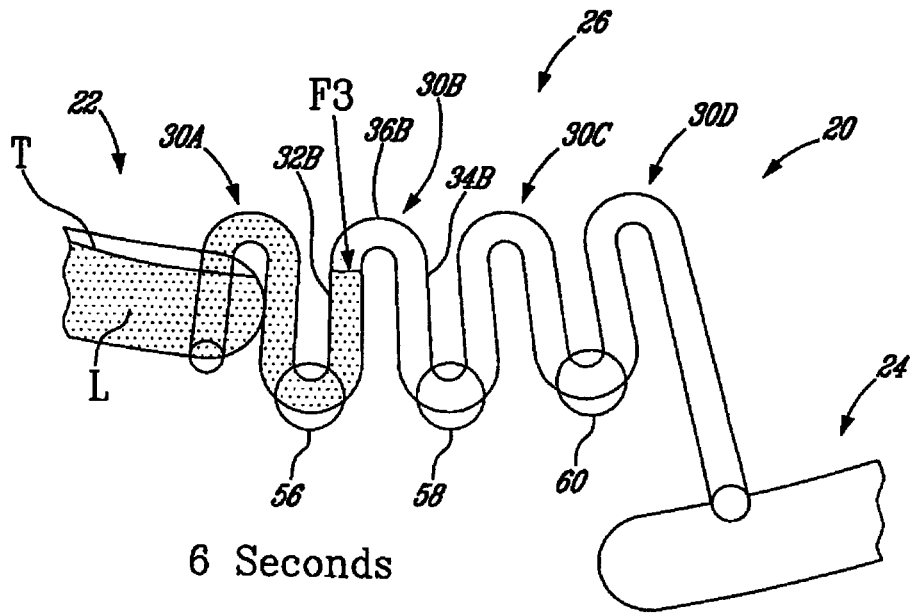
Figure 7D:
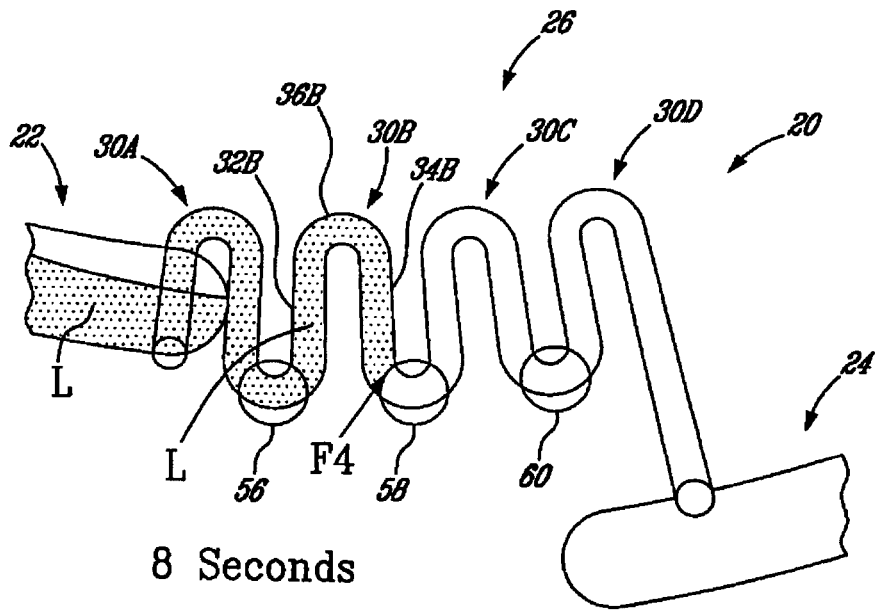
Figure 7E:
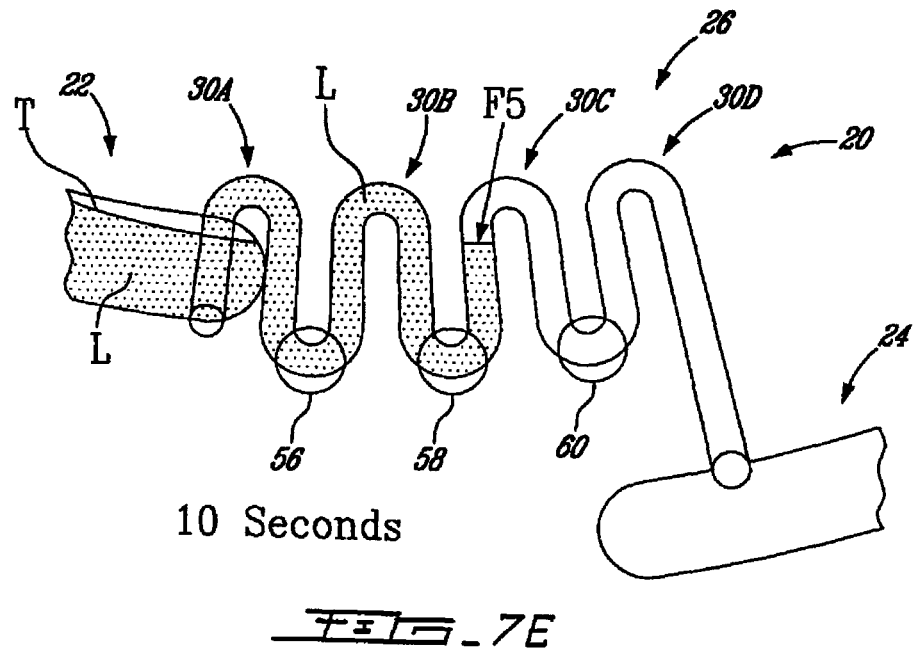
Figure 7F:
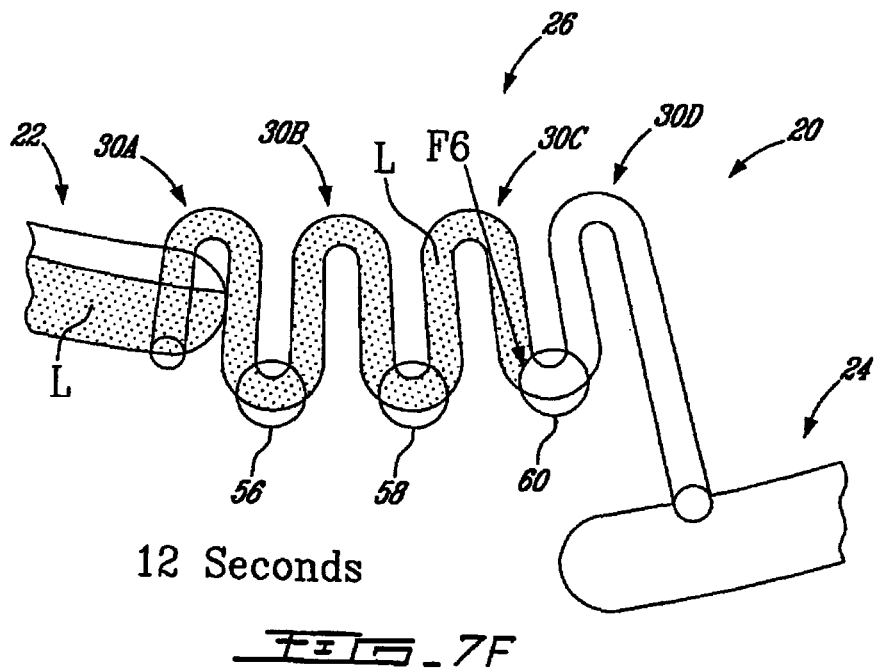
Figure 7G:
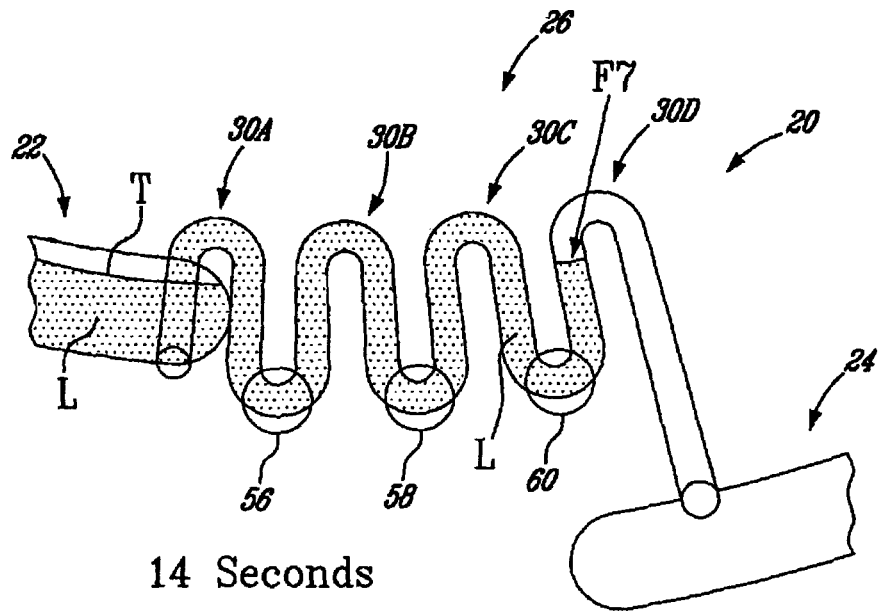
Figure 7H:
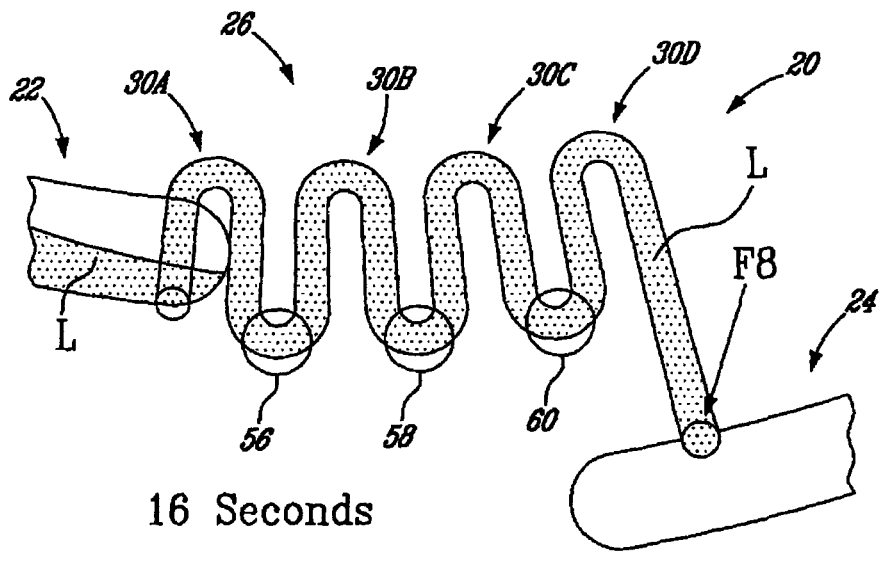
Figure 8:
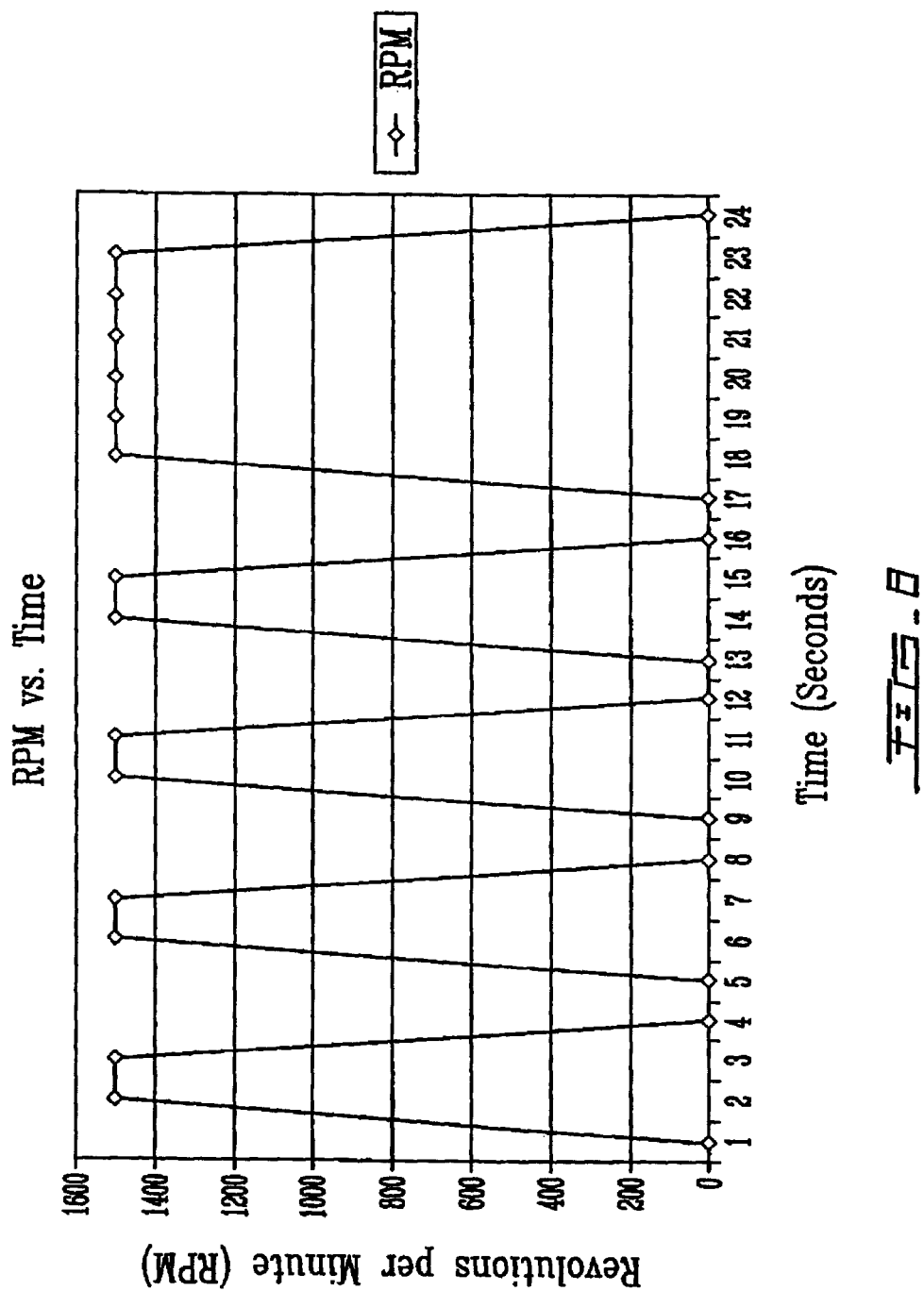
FIG. 8 illustrates the spin profile used to control the flow of liquid in the serial siphon valve system of FIGS. 7A to 7J.

In this respect FIG. 7A shows the liquid front F1 at 2 seconds; FIG. 7B shows the liquid front F2 at 5 seconds; FIG. 7C shows the liquid front F3 at 6 seconds; FIG. 7D shows the liquid front F4 at 8 seconds; FIG. 7E shows the liquid front F5 at 10 seconds; FIG. 7F shows the liquid front F6 at 12 seconds; FIG. 7G shows the liquid front F7 at 14 seconds; FIG.

Figure 7I:
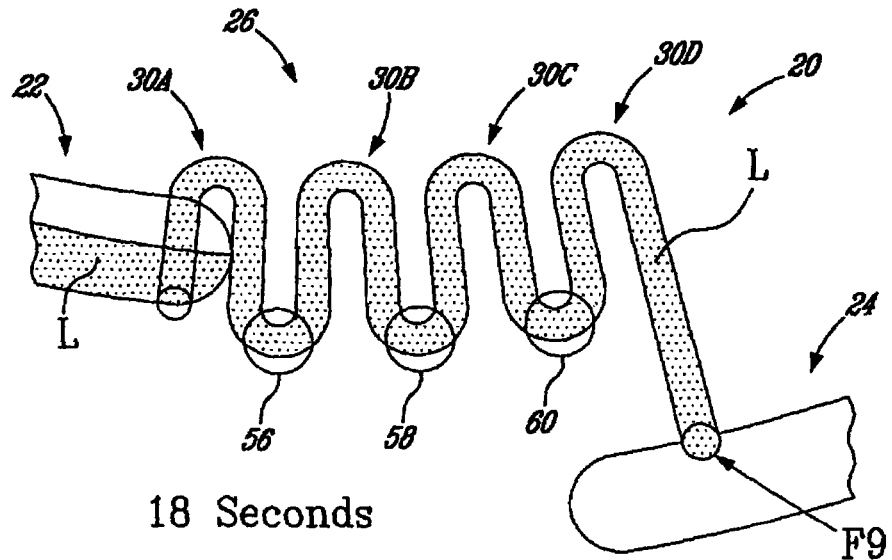
Figure 7J:
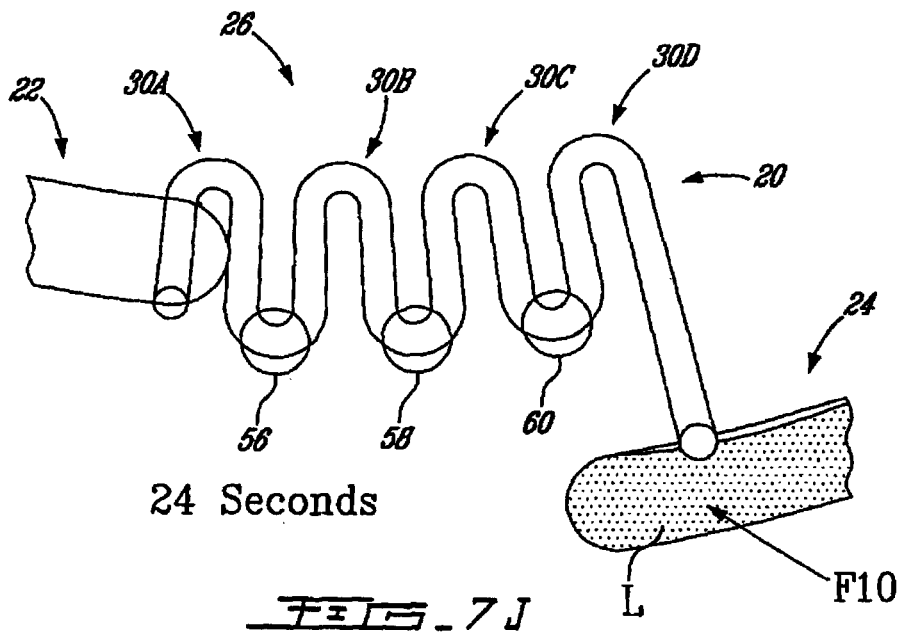

7H shows the liquid front F8 at 16 seconds; FIG. 7I shows the liquid front F9 at 18 seconds; FIG. 7J shows the liquid front F10 at 24 seconds.

Materials and Methods:

The design of the disk was accomplished by the use of SolidWorks 2005 computer aided design software from Solidworks Corporation (Concord, Mass.). A rotating disk for the demonstration of the serial siphon concept was constructed by the use of standard compact disks (CD 1.1 mm thick) and digital versatile disks (DVD, 0.6 mm thick) purchased from U-Tech Media Corporation (Taiwan). The disks were machined by the use of a QuickCircuit 5000 computer numerical control system from T-Tech, Inc. (Norcross, Ga.). A 100 micrometer thick transfer adhesive called Flexrnount DEM 200 Clear, V-95 150 Poly H-9 V-95-4, from Flexcon, Inc. (Spencer, Mass.) was used to bond the disks together. Cutting of this adhesive to define microfluidic channels was done with a CE2000-60 cutting plotter from Graphtec America (Santa Ana, Calif.). A "Sidewinder" large roller laminator from Desert Laminator (Palm Springs, Calif.) was used to press the disk assembly together. A spinstand was assembled to rotate and test the design as previously described and illustrated (Jia et al., 2006, Sensors Actuators B, 114:173-181). It consisted of a servo motor model PMB21B-00114-00, a driver model PC3406Ai-001-E, and ToolPAC control software. All of the items were made by Pacific Scientific (Rockford, Ill.). A microfluidic disk to be tested is placed on an aluminum platen coupled to the motor shaft and is locked in place by a plastic screw.

With a vision system mounted on the spinstand, we were able to view a sequence of color images of the area of interest on the disk in real time (while rotating) and store the captured frames on a computer. The digital video recording system was composed of a camera model A301bc made by Basler (Germany) with a resolution of 640×480 pixels; able to capture a maximum of 80 frames per second. A Computer (Japan) brand 10× zoom lens was mounted on the camera and focused on the surface for the rotating disk. A strobe light model MVS-4200 from PerkinElmer (Fremont, Calif.) was set to 6 µs duration and used to help capture a clear image of the disk while rotating. A retro-reflective fiber optic sensor model D10 made by Banner (Minneapolis, Minn.) was deployed right above the edge of the rotating disk. In order to generate synchronized signals, a white square mark (2 mm×2 mm) was placed on the edge of the disk and aligned such that it fell immediately below the light spot emitted from the fiber optic sensor when the microfluidic structures of interest on the rotating disk came into view of the camera. Thus, whenever this square came under the light beam of the sensor, a pulse was sent to the video capture board which then immediately triggered the camera and strobe light to acquire one image frame per revolution.

Procedure:

The disk 12 is a stratified assembly of three machined polycarbonate disks and two cut adhesives as previously described with reference to FIG. 5.

The different components of the disk 12 were aligned and pressed together to form an assembly. All the fluidic surfaces of the disk 12 were hydrophilic. The upstream chamber 22 was filled with water colored with red food coloring. The spin profile depicted in FIG. 8 was applied to the filled disk 12.

Results:

The serial siphon valves 30A, 30B, 30C, 30D are separated by capillary valves (or "stoppers") 56, 58 and 60. It was observed that the liquid L in the upstream chamber 22 traveled along the serial siphon valve conduit 26 as seen in the sequence of the drawings of FIGS. 7A-7J. When a first high centripetal acceleration is applied to the system, the liquid L from the upstream (dispensing) chamber 22 is blocked into the first siphon valve 30A (in canal 32A at the precipice of bend 36A) as soon as the liquid level in the siphon canal reaches the level T of the liquid L in the upstream chamber 22 at liquid front F1 (see FIGS. 7A and 8 at 2 seconds). When the centripetal acceleration is decreased below the capillary force intensity of the siphon valve 30A, the liquid L therein is moved by the capillary force past bend 36A and through outlet canal 34A until it reaches the first capillary valve 56 where the liquid stops L With reference to FIGS. 7B and 8 at 5 seconds, the liquid front F2 is at the precipice of bend 38 which includes the valve 56. During the second high centripetal acceleration, the first stopper or valve 56 bursts i.e. is traversed by the liquid L but, because of high centripetal acceleration, the second siphon valve 30B does not prime (see FIGS. 7C and 8 at 6 seconds). In other words, the liquid front F3 stops within inlet canal 32B (at the precipice of bend 36B) when it is at the level T of the liquid L in the chamber 22. Priming of the second siphon valve 32B occurs only when the centripetal acceleration is reduced again. Hence, with reference to FIGS. 7D and 8 at 8 seconds, the liquid L flows via bend 36B into canal 34B and stops (F4) at the second capillary valve 58. Priming of any subsequent siphon valve (30C and 30D in this case) occurs based on the same principle as illustrated in the steps shown in FIGS. 7E, 7F, 7G, 7H, 7I, 7J and FIG. 8 from 9 to 24 seconds. The spin sequence illustrated in FIGS. 7I, 7J and 8 from 17 to 24 seconds is made longer simply to allow aspiration of all the liquid L in the serial siphon valve conduit 26 to fill the downstream receiving chamber 24.

The skilled artisan will readily understand that the centrifugation times presented above for the different cycles is not critical and may be modified without altering the general concept detailed herein.

Conclusion

It was possible to control the downstream flow of a liquid from an upstream chamber to a downstream chamber on a disk by applying multiple cycles of rotation/stopping. The radial distance between the two chambers was reduced (relative to the standard siphon design) by the use of the above described serial siphon-capillary valve design (namely serial siphon valve conduit).

It should be noted that the various features of the various devices and methods described herein can be combined in other ways by one having skill in the art so as to provide other non-illustrated embodiments within the scope of the invention.

It is to be understood that the invention is not limited in its application to the details of construction and parts illustrated in the accompanying drawings and described hereinabove. The invention is capable of other embodiments and of being practiced in various ways. It is also to be understood that the phraseology or terminology used herein is for the purpose of description and not limitation. Hence, although the present invention has been described hereinabove by way of embodiments thereof, it can be modified, without departing from the spirit, scope and nature of the subject invention.

What is claimed is:

1. A centripetal microfluidic device comprising:
   a rotatable disk defining a platform having a circumference and a central hole for receiving an actuator for being rotated thereby; and
   a microfluidic network formed in said platform comprising:
      a longitudinal curved upstream dispensing chamber near said circumference;

a longitudinal curved downstream receiving chamber being radially outward relative to said upstream chamber; and a serial siphon valve conduit interposed therebetween and comprising an inlet aperture in fluid communication with said dispensing chamber and an outlet aperture in fluid communication with said receiving chamber, said serial siphon valve conduit comprising a sinuous configuration between said inlet and outlet apertures defining a series of co-radial siphon valves separated by capillary valve structures, said series of co-radial siphon valves defining radially inward bends and radially outward bends, said capillary valve structures being respectively positioned at and contiguous with respective said bends thereby enlarging the spatial structure of said bends, wherein when applying a centripetal force to said microfluidic network, a fluid within said network flows in the downstream direction, each said capillary valve structure configured for blocking fluid movement when the capillary force of said capillary valve structure overcomes the centripetal force.

2. A centripetal microfluidic device according to claim 1, wherein said disk comprises an assembly of interfaced disk members.

3. A centripetal microfluidic device according to claim 1, wherein said upstream chamber comprises a pair of opposite walls, one said wall being radially outward of the other said wall, said inlet being positioned near said radially outward wall.

4. A centripetal microfluidic device according to claim 1, wherein said downstream chamber comprises a pair of opposite walls, one said wall being radially inward of the other said wall, said outlet being positioned near said radially inward wall.

5. A centripetal microfluidic device according to claim 1, wherein said siphon valves are integral with said capillary valve structures.

6. A centripetal microfluidic device according to claim 1, wherein a said siphon valve comprises a pair of adjacent canal branches, said bend interposed therebetween.

7. A centripetal microfluidic device according to claim 1, wherein said bend is radially inward relative to said pair of canal branches.

8. A centripetal microfluidic device according to claim 1, wherein said another bend is radially outward relative to said bend interposed between said adjacent canal branches.

9. A centripetal microfluidic device according to claim 1, further comprising the actuator.

10. A centripetal microfluidic device according to claim 1, wherein said radially inward bends are positioned generally along the same inner arc, said radially outward bends being positioned generally along the same outer arc, said outer arc being radially inwards relative to said downstream receiving chamber.

11. A centripetal microfluidic device according to claim 10, wherein said inner arc is radially inwards relative to said upstream dispensing chamber.

\* \* \* \* \*